United States Patent [19]

Ray et al.

[11] Patent Number: 5,649,945

[45] Date of Patent: Jul. 22, 1997

[54] SPINAL ANULUS CUTTER

[75] Inventors: Charles D. Ray, Golden Valley; Eugene A. Dickhudt, New Brighton, both of Minn.

[73] Assignee: RayMedica, Inc., Bloomington, Minn.

[21] Appl. No.: 324,143

[22] Filed: Oct. 17, 1994

[51] Int. Cl.$^6$ ............................................. A61B 17/32
[52] U.S. Cl. ................................... 606/167; 606/184
[58] Field of Search .............................. 606/166, 167, 606/181, 184, 185; 30/113.1, 121, 315, 316, 329, 332; 128/759, 898

[56] References Cited

U.S. PATENT DOCUMENTS

| | | | |
|---|---|---|---|
| 959,450 | 5/1910 | Bridgeman | 30/113.1 |
| 1,551,815 | 9/1925 | Ferguson | 30/113.1 |
| 1,573,681 | 2/1926 | Daireaux. | |
| 4,150,675 | 4/1979 | Comparetto | 30/316 |
| 5,056,223 | 10/1991 | Buck et al. | 30/113.1 |
| 5,078,724 | 1/1992 | Takase | 606/167 |
| 5,186,178 | 2/1993 | Yeh et al. | 606/167 |
| 5,306,309 | 4/1994 | Wagner et al. | |

FOREIGN PATENT DOCUMENTS 1003828  3/1983  U.S.S.R. .................... 606/167

*Primary Examiner*—William Lewis
*Attorney, Agent, or Firm*—Kinney & Lange, P.A.

[57] ABSTRACT

A spinal anulus cutter for cutting a multisided flap in an encapsulating ligament, such as an anulus of a human intervertebral disc, to provide access to an interior space or material surrounded by the ligament. The spinal anulus cutter is characterized by a knife blade comprised of a plurality of walls which are connected together to define a closed side and an open side. Further, a cutting edge is formed at the forward edge of the walls which is configured to cut the multisided flap in the ligament when an axial force is transmitted to the knife blade in a direction towards the cutting edge. The flap will conform in shape and size to the form of the knife blade, whereby the open side of the knife blade will not cut the ligamentary tissue.

22 Claims, 6 Drawing Sheets

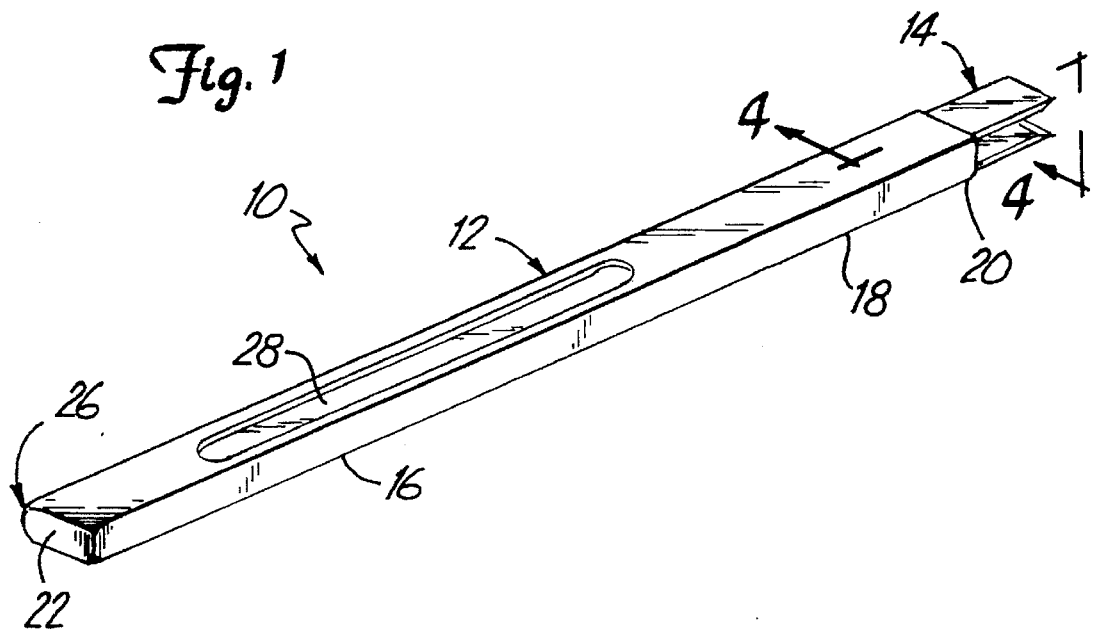
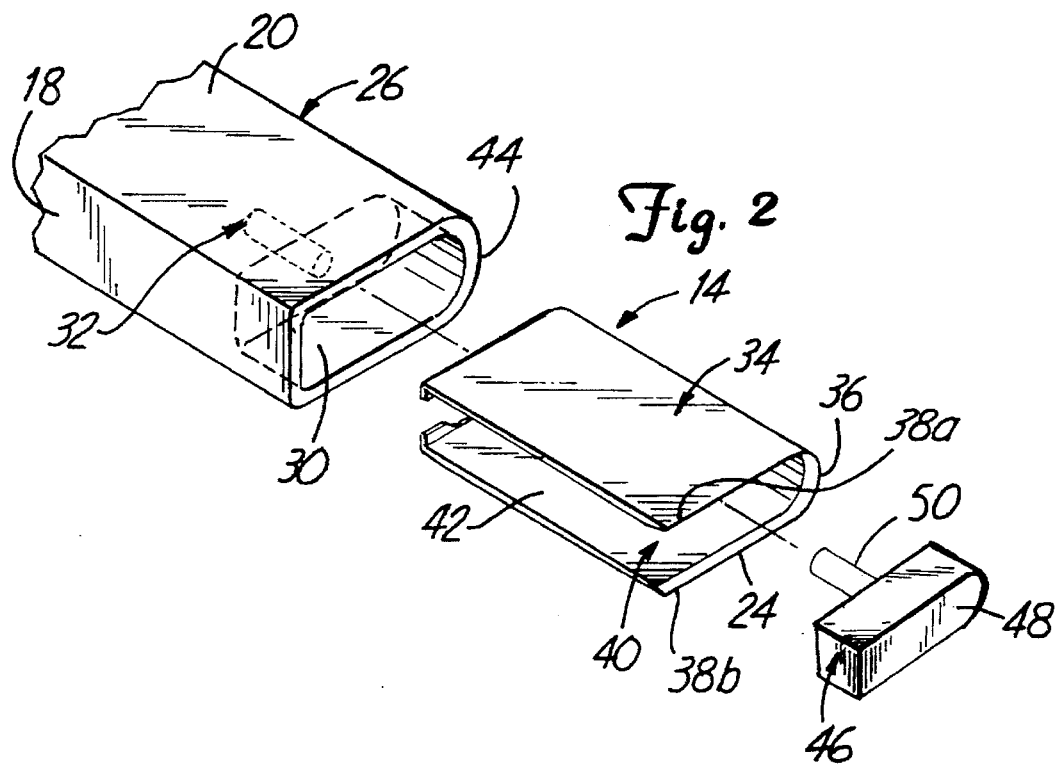

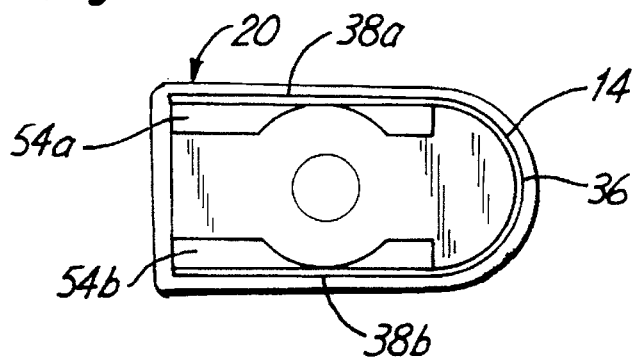
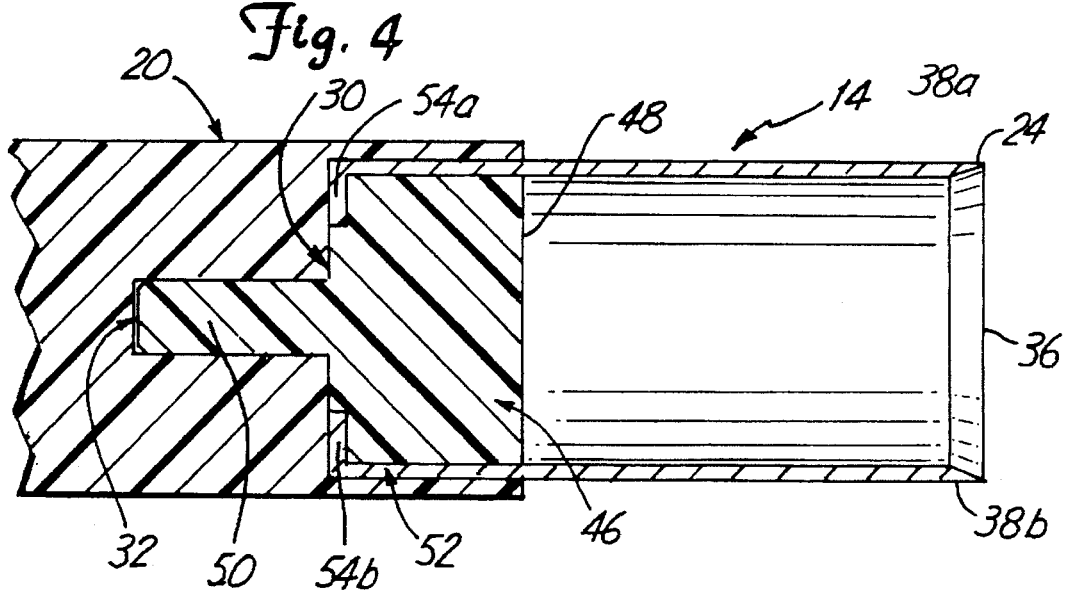

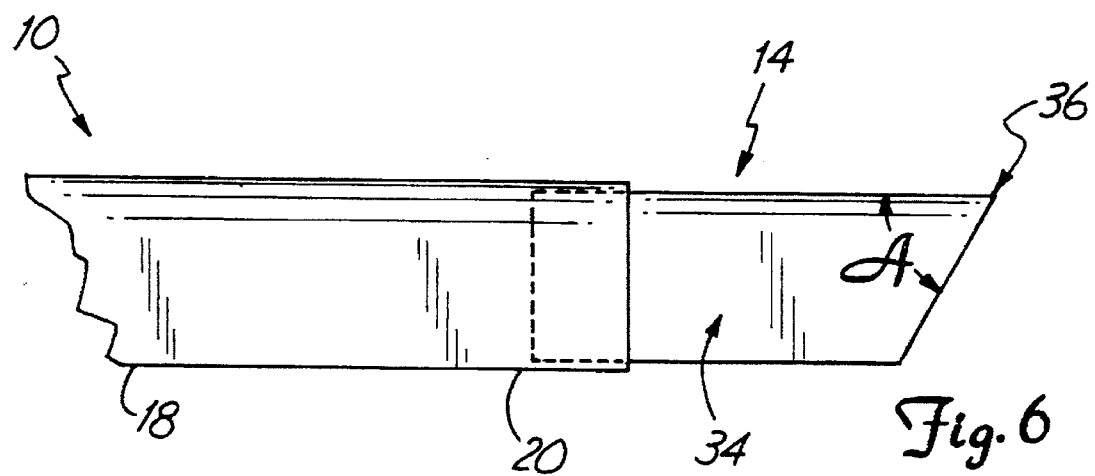

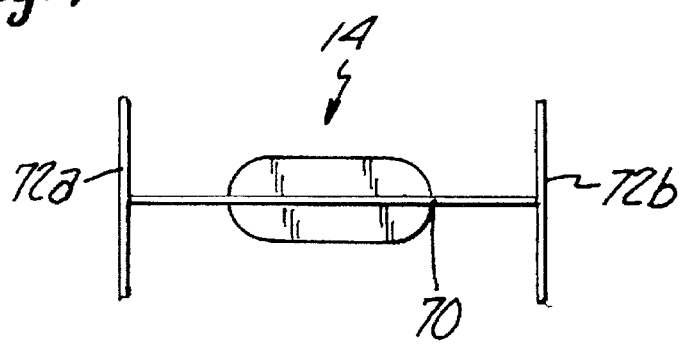
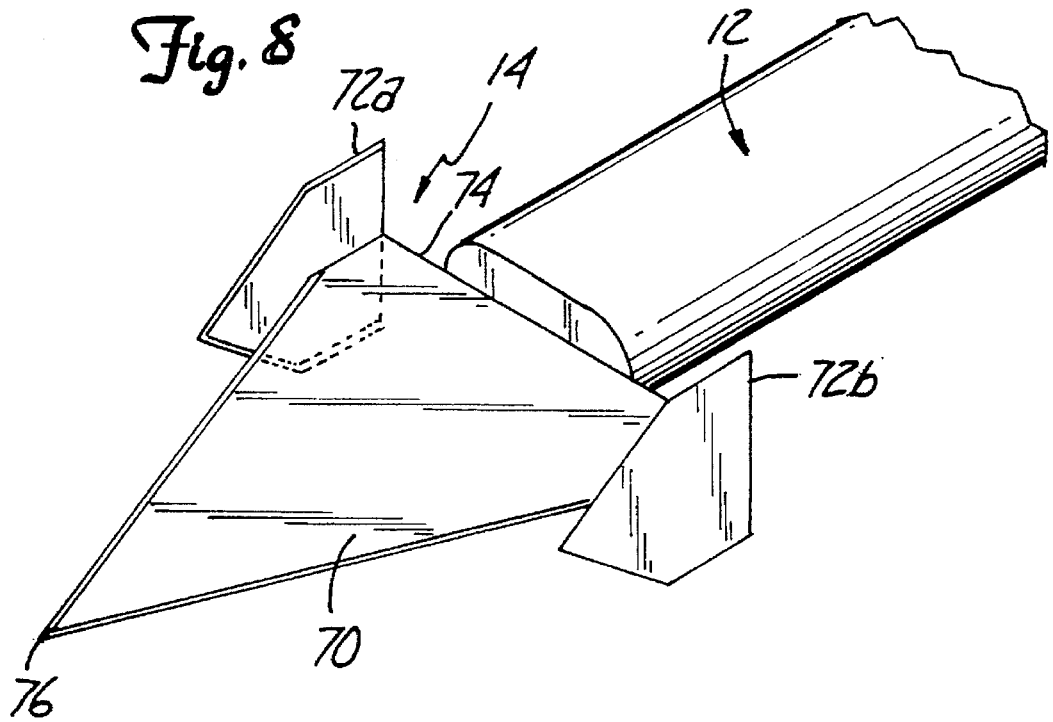

SPINAL ANULUS CUTTER

BACKGROUND OF THE INVENTION

Co-pending patent application entitled "Prosthetic Spinal Disc Nucleus" and "Method for Surgical Implantation Of A Prosthetic Spinal Disc Nucleus" were filed on the same day as the present application and are assigned to the same assignee.

The present invention concerns a surgical tool for piercing an anulus of a human intervertebral disc. More particularly, it relates to an spinal anulus cutter for cutting a flap into the anulus for any reason, for example as part of a discectomy surgery or prior to surgical removal of a spinal discal nucleus, e.g. for herniated discs or implantation of a prosthetic spinal disc nucleus body.

The vertebrate spine is the axis of the skeleton on which all of the body parts "hang". In humans, the normal spine has seven cervical, twelve thoracic and five lumbar segments. The lumbar spine sits upon the sacrum, which then attaches to the pelvis, in turn supported by the hip and leg bones. The bony vertebral bones of the spine are separated by intervertebral discs, which act as joints but allow known degrees of flexion, extension, lateral bending, and axial rotation.

The typical vertebra has a thick anterior bone mass called the vertebral body, with a neural (vertebral) arch that arises from the posterior surface of the vertebral body. The centra of adjacent vertebrae are supported by intervertebral discs. Each neural arch combines with the posterior surface of the vertebral body and encloses a vertebral foramen. The vertebral foramina of adjacent vertebrae are aligned to form a vertebral canal, through which the spinal sac, cord and nerve rootlets pass. The portion of the neural arch which extends posteriorly and acts to protect the spinal cord's posterior side is known as the lamina. Projecting from the posterior region of the neural arch is a midline spinous process.

The intervertebral disc primarily serves as a mechanical cushion between vertebral bones, permitting controlled motion within vertebral segments of the axial skeleton. The normal disc is a unique, mixed structure, comprised of three component tissues: the nucleus pulpous ("nucleus"), the anulus fibrosus ("anulus") and two vertebral end plates. The two vertebral end plates are composed of thin cartilage overlying a thin layer of hard, cortical bone which attaches to the spongy, richly vascular, cancellous bone of the vertebral body. The end plates thus act to attach adjacent vertebrae to the disc. In other words, a transitional zone is created by the end plates between the malleable disc and the bony vertebrae.

The anulus of the disc is a tough, outer fibrous ring which binds together adjacent vertebrae. This fibrous portion, which is much like a laminated automobile tire, is generally about 10 to 15 millimeters in height and about 15 to 20 millimeters in thickness. The fiber layers of the anulus consist of fifteen to twenty overlapping multiple plies, and are inserted into the superior and inferior vertebral bodies at roughly a 40 degree angle in both directions. This configuration particularly resists torsion, as about half of the angulated fibers will tighten when the vertebrae rotates in either direction, relative to each other. The laminated plies are less firmly attached to each other.

Immersed within the anulus, positioned much like the liquid core of a golf ball, is the nucleus. The healthy nucleus is a largely gel-like substance having a high water content, and like air in a tire, serves to keep the anulus tight yet flexible. The nucleus-gel moves slightly within the anulus when force is exerted on the adjacent vertebrae while bending, lifting, etc.

The spinal disc may be displaced or damaged due to trauma or a disease process. A disc herniation occurs when the anulus fibers are weakened or torn and the inner tissue of the nucleus becomes permanently bulged, distended, or extruded out of its normal, internal anulus confines. The mass of a herniated or "slipped" nucleus tissue can compress a spinal nerve, resulting in leg pain or loss of muscle control and even paralysis. Alternatively, with discal degeneration, the nucleus loses its water binding ability and deflates, as though the air had been let out of a tire. Subsequently, the height of the nucleus decreases causing the anulus to buckle in areas where the laminated plies are loosely bonded. As these overlapping laminated plies of the anulus begin to buckle and separate, either circumferential or radial anular tears may occur, which may contribute to persistent and disabling back pain. Adjacent, ancillary spinal facet joints will also be forced into an overriding position, which may create additional back pain.

To alleviate pain from a herniation, it is usually necessary for the surgeon to access the nucleus area within the anulus. This may be to perform discectomy surgery, remove the herniated anulus or nucleus, or implant a prosthetic nucleus device. To access the nucleus, the surgeon is required to cut through and/or remove at least a portion of the anulus. A surgical concern, not previously addressed, is the potential damage imparted upon the anulus during this surgery.

As previously stated, the normal anular plies act to keep the anulus tight about the nucleus. During the aforementioned surgeries, a surgical knife or tool is used to completely sever some portion of the anulus and/or remove an entire section or a "plug" of the anulus tissue. When an entire section of the anulus is cut or removed, the layers making up the anulus "fray" and/or "pull back" and the constraining or tightening ability of that portion of the anulus is lost. Further, the chances of the anulus healing with restoration of full strength are greatly diminished, while the likelihood of nucleus reherniation increases. An even greater concern arises where a significant portion of the anulus is removed entirely. These problems present themselves when the anulus is incised or removed during any type of discectomy surgery. Further, the same concerns arise whenever a surgeon is required to cut through an encapsulating ligament (such as the anulus, knee, shoulder, etc.) to access the space or material surrounded by the ligament. A more desirable solution is to leave the ligament or anulus at least partially intact during and after surgery.

Preserving the integrity of the anulus enhances the potential for physical healing in the disc area. As part of most disc related surgeries, a surgical tool must be employed to pierce the anulus to provide access to the area. Therefore, a substantial need exists for a surgical tool having the ability to pierce the anulus in such a way as to provide access to the discal area but allow for regenerative recovery of the anular fibers afterwards, and prevent the damaging or destruction of the tightening or constraining ability of the anulus itself. Such a tool will have similar applicability to any encapsulating ligamentary area.

SUMMARY OF THE INVENTION

The invention provides a tool for cutting a flap in an encapsulating ligament, such as an anulus located in a human intervertebral disc, to provide access to a space or material, such as the nucleus, surrounded by the ligament. The spinal anulus cutter of the present invention is characterized by a knife blade that creates a sutureable, thus repairable, flap in the ligament tissue. After the spinal anulus cutter is used to cut the anulus to its full depth, that is, into the nucleus cavity, the nucleus tissue may be removed and the flap is then restored to its original anatomical position and surgically closed.

The knife blade has a plurality of connected walls. More particularly, the walls are connected so as to create an open side and a closed side. In a preferred embodiment, the walls form an arch in which the closed side is curved, or C-shaped. A cutting edge is formed at the forward end of the walls. This cutting edge is configured to substantially simultaneously cut a multisided flap in the anulus. The walls form an internal aperture to which the flap created by the knife blade corresponds in shape.

The above described spinal anulus cutter is preferably used during removal of certain herniated or degenerated discal nuclei or the posterior implantation of a prosthetic device into the intervertebral disc area. The knife blade is used to impart a multisided flap through the encapsulating ligament, such as the anulus portion of a degenerated disc. The shape of this flap is defined by the shape of the knife blade, the dimensions of which will vary. In a preferred embodiment, a handle is used to assist in properly positioning the spinal anulus cutter and in transmitting a force imparted on the proximal end of the handle in a direction toward the knife blade.

BRIEF DESCRIPTION OF THE DRAWINGS

FIG. 1 is a perspective view of the spinal anulus cutter in accordance with the present invention.

FIG. 2 is an exploded perspective view of the head of the spinal anulus cutter of the present invention.

FIG. 3 is an enlarged end view of the spinal anulus cutter of the present invention, with a mounting plug removed.

FIG. 4 is an enlarged sectional view of the spinal anulus cutter along the line 4—4 of FIG. 1.

FIG. 6 is a top view of an alternative embodiment of the knife blade of the spinal anulus cutter.

FIG. 7 is an enlarged end view of another alternative embodiment of the knife blade of the spinal anulus cutter.

FIG. 8 is an enlarged perspective view of the knife blade of FIG. 7.

DETAILED DESCRIPTION OF THE PREFERRED EMBODIMENTS

Figure 5:
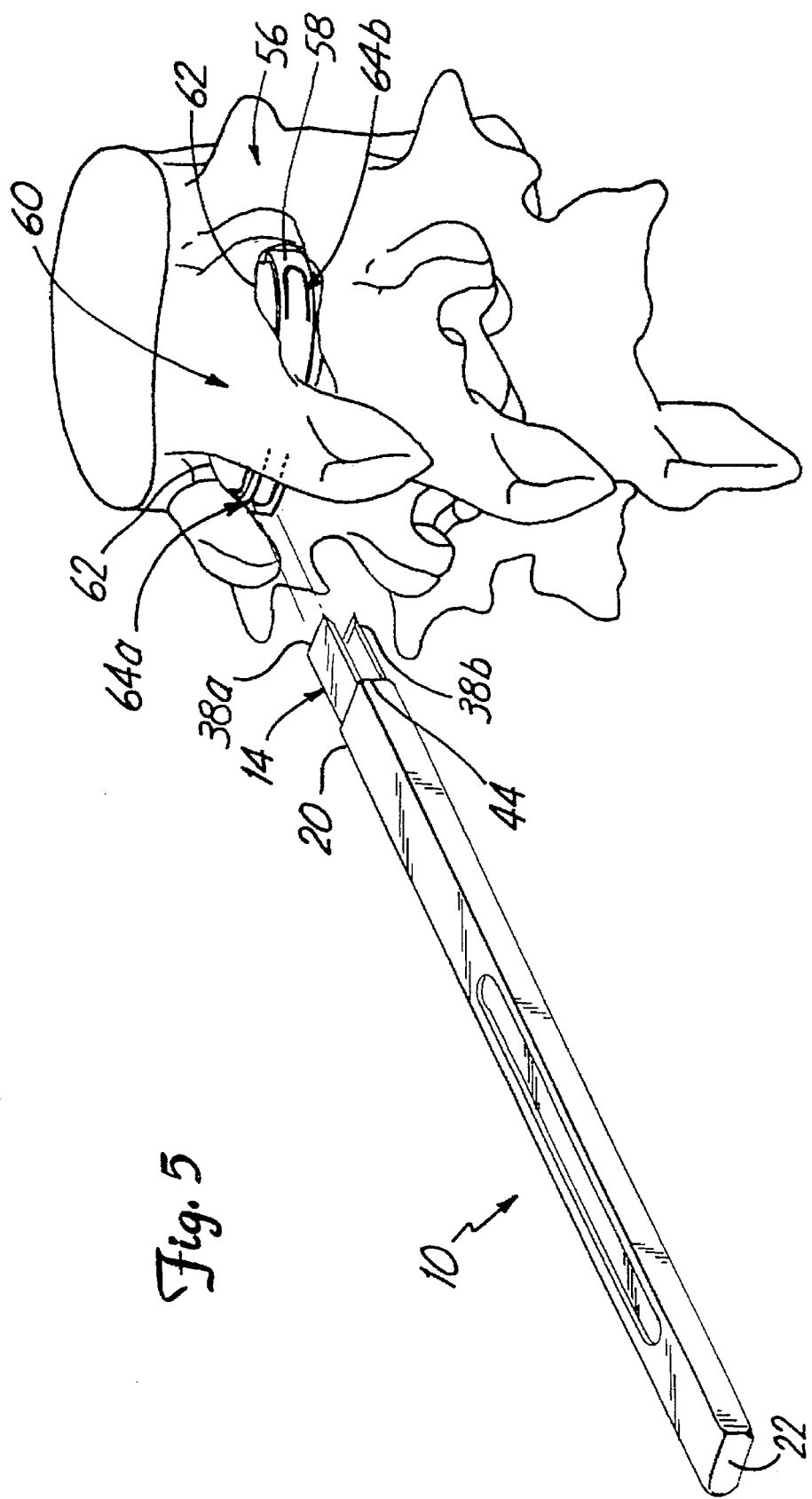
FIG. 5 is a perspective view of adjacent vertebrae having flaps created in the anulus by the spinal anulus cutter in accordance with the present invention.

A preferred embodiment of the spinal anulus cutter 10 is shown in FIG. 1. The spinal anulus cutter 10 is comprised of a handle 12 and a knife blade 14. The handle 12 has a grip 16, a shank 18 and a head 20. The grip 16 has a proximal end 22. The grip 16 is integrally attached to the shank 18 which in turn is integrally attached to the head 20. The knife blade 14 is mounted to the head 20 and extends forwardly. The knife blade 14 has a cutting edge 24 on its forward end.

The grip 16 is preferably made of a plastic material, such as polycarbonate, and is formed by standard plastic molding techniques. Other rigid, lightweight materials are equally suitable. The grip 16, which is shown in FIG. 1 as being a substantially rectangular cylinder, preferably has an axial length of about 200 millimeters (8 inches), a width of about 14 millimeters (0.55 inches) and thickness of about 8 millimeters (0.3 inches). For identification purposes, the grip 16 is provided with a rounded side 26, which corresponds with a rounded side of the knife blade 14. While details of the knife blade 14 are provided below, it is sufficient to note that the curved side 26 allows a user of the spinal anulus cutter 10 to identify the orientation of the knife blade 14 by "feeling" the rounded side 26 of the grip 16. Any other shape, such as circular, square, etc. or size which promote the simple grasping and handling of the spinal anulus cutter 10 can be used.

The proximal end 22 of the grip 16 is preferably relatively flat in a plane perpendicular to the axial length of the handle 12, but can also be rounded. Additionally, a uniform indentation 28 is provided along either side of the grip 16. The indentation 28 is preferably obround in configuration and has a length of approximately 125 millimeters (5 inches). The indentation 28 is provided to assist in grasping the handle 12 and to provide an area for various manufacturer nomenclature.

The shank 18 is integrally attached to the grip 16 and extends in an axial fashion therefrom. In the preferred embodiment, the shank 18 and the grip 16 are manufactured as a single piece. However, the shank 18 and the grip 16 can be produced as separate bodies, later mounted to one another via various mounting techniques. The shank 18 has an axial length of about 75 millimeters (3 inches) and a width and thickness similar to that of the grip 16. Further, the shank 18 has a rounded side (not shown) corresponding with the rounded side 26 of the grip 16. Alternatively, other geometrical configurations, such as circular or square, can be used. Similarly, any other length, either longer or shorter, is acceptable so long as sufficient clearance between the knife blade 14 and the proximal end 22 of the grip 16 is provided.

The shank 18 is preferably made of a plastic material, such as polycarbonate, similar to that of the grip 16. Alternatively, other surgically safe materials, such as aluminum, may be employed which maintains the rigidity of the shank 18 during use.

The shank 18 is integrally attached to the head 20. In the preferred embodiment, the head 20 and shank 18 are formed as a single piece. However, the head 20 and the shank 18 may be produced separately and later mounted via various mounting techniques.

The head 20 is preferably made of a plastic material, such as polycarbonate, and extends axially from the shank 18. As shown in FIG. 2, the head 20 conforms in shape to the shank 18, being generally rectangular with a rounded side 26. The head 20 has an opening 30 for receiving the knife blade 14. The opening 30 is of a configuration generally conforming to the outer surface of the head 20. In other words, the opening 30 is of a generally rectangular shape with one side being arcuate. The opening 30 is approximately 15 millimeters (0.5 inches) deep. A bore 32 extends rearwardly from the opening 30 in the head 20. The bore 32 is cylindrical in shape, having a diameter of about 3 millimeters (0.125 inches) and a length of about 15 millimeters (0.5 inches).

The knife blade 14 nests within the opening 30 of the head 20 and is comprised of a plurality of walls connected to one another. In a preferred embodiment, a continuous wall 34 is formed, extending forwardly from the head 20. The cutting edge 24 is formed at the forward edge of the wall 34 and has a cutting angle of approximately 22° or less. The continuous wall 34 is formed to approximate an arch shape having a closed side 36, a first extending side 38a and second extending side 38b, and an open side 40. In the preferred embodiment, the closed side 36 is curved to generally form a C-shape.

More specifically, in the preferred embodiment, the closed side 36 of the continuous wall 34 is defined by a 180 degree arc from which the first extending side 38a and the second extending side 38b project parallel to one another. The side 40 opposite the closed side 36 is open. With this configuration, the knife blade 14 creates an aperture 42 defined by the internal side of the continuous wall 34. The flap formed by the knife blade 14 will conform in shape and size with the aperture 42.

The distance between the first extending side 38a and the second extending side 38b is approximately 6 millimeters (0.25 inches). The radius of curvature of the closed, curved side 36 is approximately 3 millimeters (0.125 inches). As shown in FIG. 2, the blade wall 34 nests within the head 20. When the knife blade 14 is properly positioned, the length of the aperture 42, running from a leading edge 44 of the head 20 to the cutting edge 24 of the knife blade 14, is approximately 20 millimeters (0.75 inches). Finally, the width of both the first extending side 38a and the second extending side 38b is approximately 13 millimeters (0.5 inches).

Alternatively, the preferred knife blade 14 may employ a variety of dimensions depending upon the desired application. For example, the above described dimensions are preferable for prosthetic implantation surgery. However, for a herniation discectomy, the first extending side 38a and the second extending side 38b of the knife blade 14 will preferably have a width of 8 millimeters (0.575 inches).

While the knife blade 14 has been described as preferably having a generally curved or C-shape, other similar configurations are acceptable. For example, the closed side 36 need not be curved and instead may be flat, angled or serrated. In addition, other dimensions for the knife blade 14 may be employed so long as at least one multisided flap of a size sufficient to provide access to the nucleus is substantially simultaneously cut by the cutting edge 24. Basically, this requires that the knife blade 14 have at least two sides 38a and 38b which are connected on one side 36 and open on the other 40. As the knife blade 14 passes through the encapsulating ligament, such as this anulus, the open side 40 will not cut the ligament material and thus forms the "pivot point" for the flap. The cutting edge 24 is therefore a pair of spaced end points connected by a continuous, nonlinear path or wall. Alternatively, a plurality of flaps may be formed, such as by an "X"-shaped or "Y"-shaped knife blade.

The knife blade 14 is preferably made of 420 stainless steel. Alternatively, any other type of surgically safe metal can be used, such as 174 stainless steel, titanium, surgical steel, etc.

The knife blade 14 is mounted within the opening 30 of the head 20 by way of a plug 46. The plug 46 is comprised of a distal member 48 and a proximal member 50. The proximal member 50 is of a size and configuration similar to the bore 32 of the head 20. The distal member 48 is of a size and configuration similar to the opening 30.

As shown in FIGS. 3 and 4, the knife blade 14 has a proximal end 52 from which a first tab 54a and a second tab 54b extend inwardly. The first tab 54a and the second tab 54b project approximately 0.03 inches from the knife walls. Notably, the plug 46 is not depicted in FIG. 3 to better illustrate the shape of the first tab 54a and the second tab 54b.

After the knife blade 14 is placed within the opening 30 of the head 20, the plug 46 is then inserted into the head 20 such that the proximal member 50 of the plug 46 nests within the bore 32 of the head 20. The distal member 48 of the plug 46 comes in contact with the first tab 54a and the second tab 54b, thus holding the knife blade 14 in place. In addition to a frictional fit, a solvent is used to maintain the plug 46 and knife blade 14 in this final position.

As shown in FIG. 5, the spinal anulus cutter 10 is used to impart flaps through an anulus portion of a human disc. Basically, a human discal area 56 has an anulus 58 which surrounds a nucleus (not shown). The disc area 56 is posteriorly protected by a lamina bone 60. To provide sufficient access to the anulus 58, a portion of the lamina bone 60 is removed via a bilateral laminectomy, creating two arches 62 in the lamina 60.

The spinal anulus cutter 10 is brought into contact with the exposed anulus 58. More specifically, the knife blade 14 is guided into the discal area 56 through one of the lamina arches 62 until contacting the anulus 58. To minimize any damage to the anulus 58 and to maintain its constraining ability about the discal area 58, the knife blade 14 is orientated such that the first extending side 38a and the second extending side 38b approximately match the orientation of the plies comprising the anulus 58. A flap 64a or 64b is formed in the anulus by imparting a sharp axial force, via a mallet or similar device, on the proximal end 22 of the handle 12. The shape of the flap 64a or 64b will correspond with the shape of the knife blade 14. The leading edge 44 of the head 20 prevents the knife blade 14 from projecting past the internal side (not shown) of the anulus 58. In other words, the knife blade 14 will not cut into the center of the discal area 56 after the leading edge 44 of the head 20 contacts the anulus 58. Additionally, a collar or foot may project from the external surface of the head 20 to assist in preventing passage of the knife blade 14 past the anulus 58.

The spinal anulus cutter 10 is carefully removed from the anulus 58 and the newly formed flaps 64a and 64b are then retracted in a posterior or dorsal direction to provide access to the nucleus area. After performing the desired surgery in the nucleus area, such as removing the nucleus, inserting a prosthetic, etc., the flaps 64a and 64b are closed by a surgical staple suture, or other means such as "tissue glue" (a human plasma cryoprecipitate and thumbian mixture, or equivalent).

The flap 64a or 64b formed by the spinal anulus cutter 10 of the present invention is advantageous in that it does not completely sever an entire section of the anulus 58. Additionally, the majority of the cut will correspond with the direction of the plies making up the anulus 58. The flap 64a or 64b therefore causes minimal damage to the anulus 58, allowing the healing process to begin and further does not destroy the constraining ability of the anulus 58. While the spinal anulus cutter 10 has been described as forming a flap in the anulus 58, the spinal anulus cutter 10 will perform a similar function on any other encapsulating ligament.

To aid the spinal anulus cutter 10 in piercing the anulus tissue, an alternative embodiment, the top view of which is shown in FIG. 6, employs knife blade 14 with a relief angle A. The continuous wall 34 of the knife blade 14 is shaped such that the cutting edge 24 angles rearwardly (i.e., toward the head 20) from the closed end 36 to the open end 40. With this relief angle, the knife blade 14 effectively has a small plane or point on the closed end 36 which initially contacts and then easily pierces the anulus or encapsulating ligament tissue. As the cutting edge 24 continues through the anulus tissue, the desired flap is formed in conjunction with the preferably curved shape of the knife blade 14. As shown in FIG. 6, the relief angle A is preferably about 30° to about 60°. Additionally, the relief angle may extend rearwardly from the open end 40 to the closed end 36. Finally, the relief angle of the cutting edge 24 may contain a number of angles and/or curves to create a sufficient cutting surface.

As previously stated, other configurations for the knife blade 14 exist, all of which cut at least one flap through the anulus 58. For example, as shown in FIGS. 7 and 8, in an alternative embodiment the knife blade 14 can assume the shape of an elongated "H". The elongated "H" knife blade 14 has a horizontal member 70 which bisects two vertical members 72a and 72b. The horizontal member 70 and the vertical members 72a and 72b extend from a base 74 which in turn is mounted to the handle 12. To facilitate simple piercing of the anulus tissue, the horizontal member 70 extends in a triangular fashion from the base 74 with a sharp tip 76 at the forward end. Similarly, the vertical members 72a and 72b each have a sharpened end 78. With this configuration, the sharp tip 76 of the horizontal member 70 first pierces the anulus tissue when the elongated H-style knife blade 14 is used. As the knife blade 14 continues forward, the vertical members 72a and 72b cut the anulus tissue, resulting in the elongated H-style cut. Thus, the anulus is provided with two flaps, above and below the cut made by the horizontal member 70, which are peeled back to expose the nucleus area. The elongated H-style flaps are advantageous in that the flaps are easily sutured.

Figure 9:
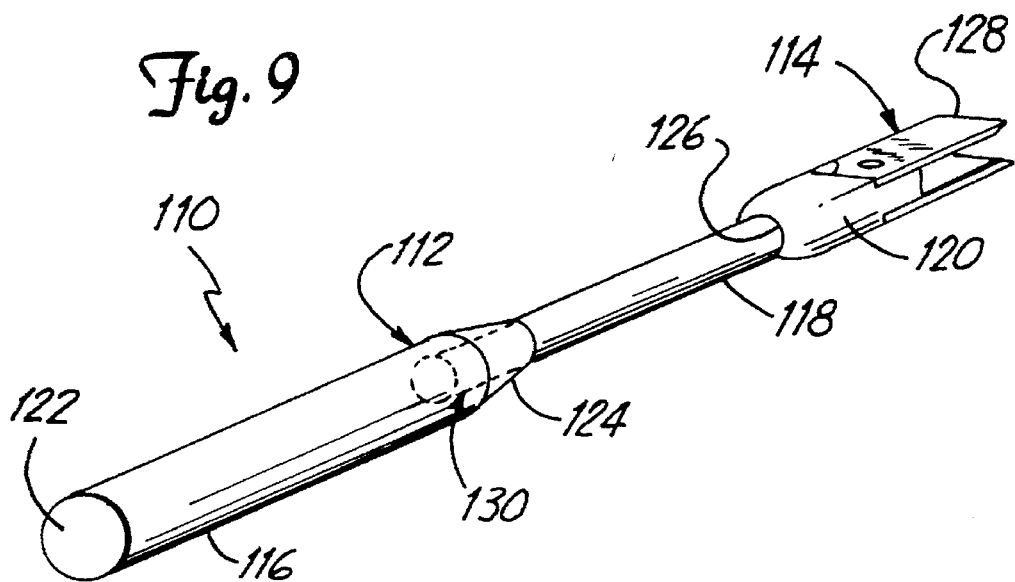
FIG. 9 is a perspective view of another alternative embodiment of the spinal anulus cutter.

A further alternative embodiment of an spinal anulus cutter 110 is shown in FIG. 9. The spinal anulus cutter 110 is comprised of a handle 112 and a knife blade 114. The handle 112 has a grip 116, a shank 118 and a head 120. The grip 116 has a proximal end 122 and a tapered end 124 in which the shank 118 nests.

The shank 118 has a distal end 126 which is integrally attached to the head 120. The knife blade 114 is mounted to the head 120 and extends forwardly. The knife blade has a cutting edge 128 on its forward end.

The grip 116 is preferably made of a plastic material and is formed by standard plastic molding techniques. Other rigid, lightweight materials are equally suitable. The grip 116, while shown as being cylindrical can assume any other shape, such as rectangular, square, etc., which promotes the simple grasping and handling of the spinal anulus cutter 110. The proximal end 122 is relatively flat in a plane perpendicular to the axial length of the handle 112. The tapered end 124 of the grip 116 has an internal bore 130 which receives the shank 118.

The shank 118 is removably mounted to the internal bore 130 of the grip 116 and extends axially therefrom. This attachment is created by a portion of the shank 118 nesting within the bore 130 of the grip 116. The diameter of the bore 130 is sized to maintain a tight, frictional fit about the shank 118. Other mounting configurations, such as glue, weld, bolt, etc., can be used. Alternatively, the shank 118 and grip 116 can be manufactured as a single piece.

The shank 118 is preferably an elongated cylinder and extends axially from the bore 130 of the grip 116 to the distal end 126. Any length is acceptable so long as sufficient clearance between the knife blade 114 and the proximal end 122 of the grip 116 is provided.

The shank 118 is preferably made of a rigid, lightweight material, such as aluminum. Alternatively, other surgically safe materials, such as plastic, may be employed which maintains the rigidness of the shank 118 during use.

The shank 118 is integrally attached to the head 120 at the distal end 126 of the shank 118. More specifically, the distal end 126 is machined down to a dimension smaller than that of the shank 118. The machined portion of the distal end 126 is placed within a bore (not shown) in the head 120. The head 120 and the distal end 126 of the shank 118 are thus frictionally attached to one another. Additionally, glue or a weld is employed to permanently fasten the head 120 and the shank 118. Alternatively, other mounting methods may be employed, such as mounting the head 120 within the distal end 126 of the shank 118, welding the two components to one another, or simply manufacturing the shank 118 and the head 120 as a single body.

Figure 10:
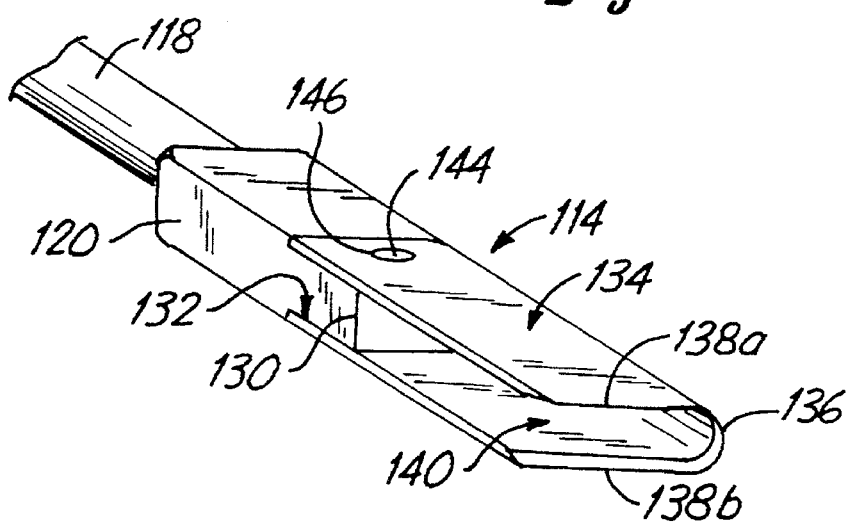
FIG. 10 is an enlarged perspective view of the head of the spinal anulus cutter of FIG. 9.

As shown in FIG. 10, the knife blade 114 extends forwardly from the head 120. The head 120 projects generally along the central axis of the shank 118 and is designed to approximate the configuration of the knife blade 114. In other words, the head 120 has curved and flat portions to correspond with the form of the knife blade 114 as described below. Additionally, the head 120 has a leading edge 130 and a continuous ridge 132 for receiving the knife blade 114. The head 120 is made of a lightweight, surgically safe material, such as aluminum.

The knife blade 114 has a continuous wall 134 defined by a closed end 136, a first extending side 138a, a second extending side 138b, and an open end 140. The closed end 136 preferably is curved or C-shaped although any other configuration capable of substantially simultaneously cutting at least one flap is acceptable.

The knife blade 114 is attached to the head 120 along the continuous ridge 132. The knife blade 114 is placed onto the ridge 132 and welded in place. To facilitate this weld, a connecting pin 144 projecting through a hole 146 in the wall 134 is used. While the knife blade 114 is described as being welded to the head 120, any other mounting method may be employed, such as glue, bolts, etc. Additionally, the head 120 and knife blade 114 may be manufactured as a single piece.

The spinal anulus cutter of the present invention is uniquely designed to provide access to the nucleus by imparting a restorable flap through the anulus tissue. By creating a flap the constraining or tightening ability of the anulus is not destroyed and the probability of full recovery is greatly enhanced. When closed, this flap will abut the anulus tissue, promoting physical healing. Further, as the design and material comprising the spinal anulus cutter are inexpensive, the tool will be disposable in practice. Finally, many other applications for the spinal anulus cutter exist in terms of providing access material located behind an encapsulating ligament structure.

Although the present invention has been described with reference to preferred embodiments, workers skilled in the art will recognize that changes may be made in form and detail without departing from the spirit and scope of the invention. For example, the entire tool can be manufactured as a single piece. Additionally, while the leading edge of the head assists the user in preventing the projection of the knife blade into the nucleus area, it is not a necessary component. The knife blade can assume any of a number of configurations, which all result in the creation of at least one multisided flap. Finally, the spinal anulus cutter can be used in a variety of surgical applications involving the piercing of encapsulating ligament-like tissue. The anulus is a type-1 collagen, and many other human parts, such as the hip, knee, shoulder, etc., are of a similar structure which can be easily pierced with the spinal anulus cutter.

What is claimed is:

1. A surgical tool for cutting a flap in an encapsulating ligament, such as an anulus of a human intervertebral disc, to provide access to an interior space or material surrounded by the ligament, the surgical tool characterized by:

a knife blade having a plurality of walls connected together to define a closed side and an open side, and having a cutting edge at a forward end of the walls, wherein a portion of the cutting edge is linear, which is configured to cut at least one multisided flap, a portion of which is linear, in a ligament when a axial force is transmitted to the knife blade in a direction toward the cutting edge; and a stop member positioned against the knife blade, perpendicular to the cutting edge for limiting cutting depth of the knife blade.

2. The surgical tool of claim 1, further comprising a handle having a first end and a second end wherein the knife blade is attached to and extends forwardly from the first end of the handle.

3. The surgical tool of claim 2 wherein the second end of the handle has a proximal edge which is flat.

4. The surgical tool of claim 1 wherein the closed side is curved.

5. The surgical tool of claim 1 wherein the plurality of walls are connected to form a continuous wall.

6. The surgical tool of claim 5 wherein the knife blade has an internal aperture defined by the continuous wall.

7. The surgical tool of claim 5 wherein the continuous wall is an arch defined by a first side and a second side extending from the closed side.

8. The surgical tool of claim 7 wherein the first side is parallel to the second side.

9. The surgical tool of claim 2 wherein the extension of the blade from the handle to the cutting edge is 20 millimeters.

10. The surgical tool of claim 1 wherein the closed side is a curve having a radius of curvature of 3 millimeters.

11. The surgical tool of claim 7 wherein the distance between the first side of the arch and the second side of the arch is 6 millimeters.

12. The surgical tool of claim 1 wherein the cutting edge has a relief angle.

13. The surgical tool of claim 12 wherein the relief angle is about 30° to about 60°.

14. The surgical tool of claim 1 wherein the continuous wall has an elongated H-shape.

15. The surgical tool of claim 1 wherein the blade is constructed of a surgically compatible material.

16. The surgical tool of claim 2 wherein the handle comprises a grip, a shank connected to the grip, and a head connected to the shank; and wherein the knife blade is connected to the head.

17. The surgical tool of claim 16 wherein the grip is removably mounted on the shank.

18. A surgical tool for cutting a flap in an encapsulating ligament, such as an anulus of a human intervertebral disc, to provide access to an interior space or material surrounded by the ligament, the surgical tool comprising:

a handle having a first end and a second end;

a knife blade attached to and extending forwardly from the first end of the handle, the knife blade defined by spaced first and second end points connected by a continuous, non-linear wall, and having a cutting edge at a forward end of the continuous wall, wherein a portion of the cutting edge is linear, which is configured to cut a multisided flap, a portion of which is linear, in the ligament when an axial force is transmitted through the handle to the knife blade in a direction towards the first end; and a stop member positioned against the knife blade, perpendicular to the cutting edge for limiting cutting depth of the knife blade.

19. The surgical tool of claim 18 further including a first side terminating at the first endpoint of the knife blade and a second side terminating at the second endpoint of the knife blade; and wherein the first side and the second side are parallel.

20. A surgical method for cutting a flap through an encapsulating ligament, such as an anulus of a human disc, the method comprising:

positioning a cutting tool, having a knife blade shaped to define a flap cutting pattern extending from a distal end of a handle, on the ligament such that the knife blade contacts the ligament; and applying an axial force to the handle to cut the flap in the ligament.

21. The surgical method of claim 20 wherein the knife blade is a plurality of walls connected together to form a closed side and an open side, and a cutting edge at a forward end of the walls.

22. The surgical method of claim 20 wherein the knife blade is a continuous, non-linear wall.

* * * * *